United States Patent
Haudenschild

(12) 
(10) Patent No.: US 6,665,647 B1
(45) Date of Patent: Dec. 16, 2003

(54) ENTERPRISE HEALTHCARE MANAGEMENT SYSTEM AND METHOD OF USING SAME

(76) Inventor: Chris A. Haudenschild, 1769 La Jolla Rancho Rd., La Jolla, CA (US) 92037

(*) Notice: Subject to any disclaimer, the term of this patent is extended or adjusted under 35 U.S.C. 154(b) by 0 days.

(21) Appl. No.: 09/343,295

(22) Filed: Jun. 30, 1999

Related U.S. Application Data

(63) Continuation-in-part of application No. 08/977,522, filed on Nov. 24, 1997.

(51) Int. Cl.$^7$ .............................................. G06F 17/60
(52) U.S. Cl. ............................................. 705/2; 705/3
(58) Field of Search ............................. 705/1–4; 707/1, 707/10, 102, 100

(56) References Cited

U.S. PATENT DOCUMENTS 4,858,121 A * 8/1989 Barber et al. .................. 705/3
5,890,129 A * 3/1999 Spurgeon ....................... 705/4

FOREIGN PATENT DOCUMENTS

WO     WO 97/37303     * 10/1997

OTHER PUBLICATIONS

Marietti, Healthcareinformatics, "Linited Access Webways . . . The reality of intranet and extranet business models", Feb. 1998.*

Suzan Eich, "Honeywell Introduces Computer network Facility for Hospitals", Dateline Chicago, IL, Dialog file 621, Accession No. 00102603, Jul. 1985.*

Gordon C. Everest, "Database Management, Objectives, Functions and Administration", McGraw Hill Inc. ISBN 01–07–019781–4, 1986.*

Deitchman eta l., "Health Industry plays catch up in Technology", The Denver Business Journal; Denver; Aug. 23, 1996, ISSN: 08937745.*

Fotsch, "Extending and enhancing existing information systems using Internet–based technologies", Healthcare Financial Management,; Westchester; Jul. 1997; ISSN: 07350732.*

* cited by examiner

*Primary Examiner*—Frantzy Poinvil
(74) *Attorney, Agent, or Firm*—Duckor Spradling Metzger; Bernard L. Kleinke

(57) ABSTRACT

The enterprise healthcare management system and method includes remotely hosting turnkey health care applications and providing enterprise users access to the turnkey applications via a public network such as the Internet.

55 Claims, 7 Drawing Sheets

ENTERPRISE HEALTHCARE MANAGEMENT SYSTEM AND METHOD OF USING SAME

CROSS-REFERENCE TO RELATED APPLICATIONS

This application is a continuation-in-part patent application of U.S. patent application Ser. No. 08/977,522, filed Nov. 24, 1997, and entitled "CLINICAL CRITICAL CARE PATH SYSTEM AND METHOD OF USING SAME", which is incorporated herein by reference.

STATEMENT REGARDING FEDERALLY SPONSORED RESEARCH OR DEVELOPMENT

Not Applicable

REFERENCE TO A "MICROFICHE APPENDIX"

Not Applicable

BACKGROUND OF THE INVENTION

1. Technical Field

The field of the present invention is healthcare management systems for healthcare enterprises. More specifically, the present invention relates to providing networked software applications for use by healthcare facilities.

2. Background Art

Primary health care is typically provided by health care enterprises. These health care enterprises are, for example, hospitals, clinics, physician groups, or even Health Maintenance Organizations (HMOs). Health care enterprises can be expansive, encompassing hundreds of doctors and many point of care facilities, or can be more modest in size. Indeed, many health care enterprises consist of only a single facility such as a hospital.

However, no matter what the size of the enterprise, all health care enterprises are coming under increased pressure to improve financial performance. With the widespread impact of managed care programs, it is critical that enterprises quickly and accurately understand their financial condition and financial trends. Further, enterprises are striving to increase efficiency while maintaining or improving patient care. For example, if the hospital stay for a particular ailment can be shortened without detriment to the patient, then the hospital can reduce costs without negatively impacting patient care. However, making such a decision requires timely, accurate, and complete information.

Most enterprises have computer systems, and many have established local area networks within their facilities. The established computer systems typically perform a variety of particular and discrete functions. For example, a hospital may have a clinical information system as described in U.S. patent application Ser. No. 08/977,522 for managing and presenting patient care management plans. The hospital may have other systems for accounting, insurance, and administrative functions. However, many of these established systems are dated or too inflexible to provide the information required to support health care enterprises in the modern managed care environment in an efficient and economical manner.

Thus, the current computer, network, and application systems used by health care enterprises are incapable of providing sufficient decision support with their existing computer facilities. Therefore, to remain viable, health care enterprises must upgrade their existing computer systems, expand networks, and possibly even re-cable. Further, the enterprise will need to phase-out existing applications as they phase-in new or updated applications. Enterprises also may need to add new applications to collect and track information not currently used.

Such a major project is beyond the financial and technical abilities of most health care enterprises. For example, upgrading computer, network, and application systems can cost millions of US dollars for an enterprise. With health care enterprises having an immediate need to improve financial performance, they are unlikely to make such an enormous expenditure in a timely manner. Thus, the enterprise must quickly improve financial performance, but is unable to expend the resources to provide the necessary information support.

Compounding the problem, health care enterprises typically have a lengthy approval cycle for making such a significant resource commitment. This approval cycle alone could take more than a year. Due to the significant expense the new system might not even be approved, leaving the enterprise uncompetitive and at risk for failure. Even after approval, the new system would have to be purchased, delivered, installed, and tested. Indeed, even if a health care enterprise can make the necessary investment, it could take one to two years, or more, to get a new system operating. During this time the enterprise's financial condition can continue to degrade, or even worsen to the point of financial failure.

Even for those enterprises willing to make the financial commitment and take the necessary time there is still significant risk. Since every enterprise has a unique mix of computers, networks, and applications, each enterprise also bears the tremendous risk associated with new system installation. In such a manner the new system can either under perform, or end up costing substantially more than expected. Either way, the new system has negatively impacted the financial performance of the enterprise, and as a result, the enterprise could be at risk for financial failure. Thereby there exists a need for a new system that can provide health care enterprises with enhanced decision support information in a cost, effective manner. The new 'system further needs to be quickly and confidently installed without burdensome expense to the enterprise. It is also desirable that existing legacy applications, computers, and networks cooperate with the new system. In such a manner the enterprise preserves prior information technology investments.

SUMMARY OF THE INVENTION

It is therefore an object of the present invention to provide a new enterprise healthcare management system for providing enhanced decision support information to a health care enterprise in a cost effective manner.

In another separate object of the present invention the new healthcare management system should utilize existing legacy applications already established at health care enterprises.

Briefly, the above and further objects are realized by providing a new enterprise healthcare management system and method of using same. The enterprise healthcare management system and method includes remotely hosting turnkey health care applications and providing enterprise users access to the turnkey applications via a public network such as the Internet.

Advantageously, the new system and method is a turnkey health care management solution. As a turnkey system, it can be quickly implemented with little risk to the enterprise. Further, since the turnkey applications are remotely hosted, the enterprise can use the turnkey applications with minimal capital investment. Thereby, the enterprise can not only upgrade existing capabilities, but add functionality not available with their existing system. For example, since the centralized turnkey system has multidisipline information relating to the enterprise, comprehensive enterprise-wide performance reports can be generated. Indeed, if multiple enterprises are managed, reports indicative of the industry are even possible.

The enterprise also can utilize existing legacy applications, thereby preserving prior IT investments. Since enterprise users access the new system via a public network such as the Internet, only minimal networking capability is needed at the enterprise. In such a manner it is likely the enterprise can also utilize existing computer and network resources.

The new turnkey health care management system also easily adjusts to changes within the enterprise. As the enterprise grows, adds facilities, sells facilities, and changes, the new system easily and cost effectively scales to facilitate the new level of need.

BRIEF DESCRIPTION OF DRAWINGS

The above mentioned and other objects and features of this invention and the manner of attaining them will become apparent, and the invention itself will be best understood by reference to the following description of the embodiment of the invention in conjunction with the accompanying drawings, wherein.

BEST MODE FOR CARRYING OUT THE INVENTION

Figure 1:
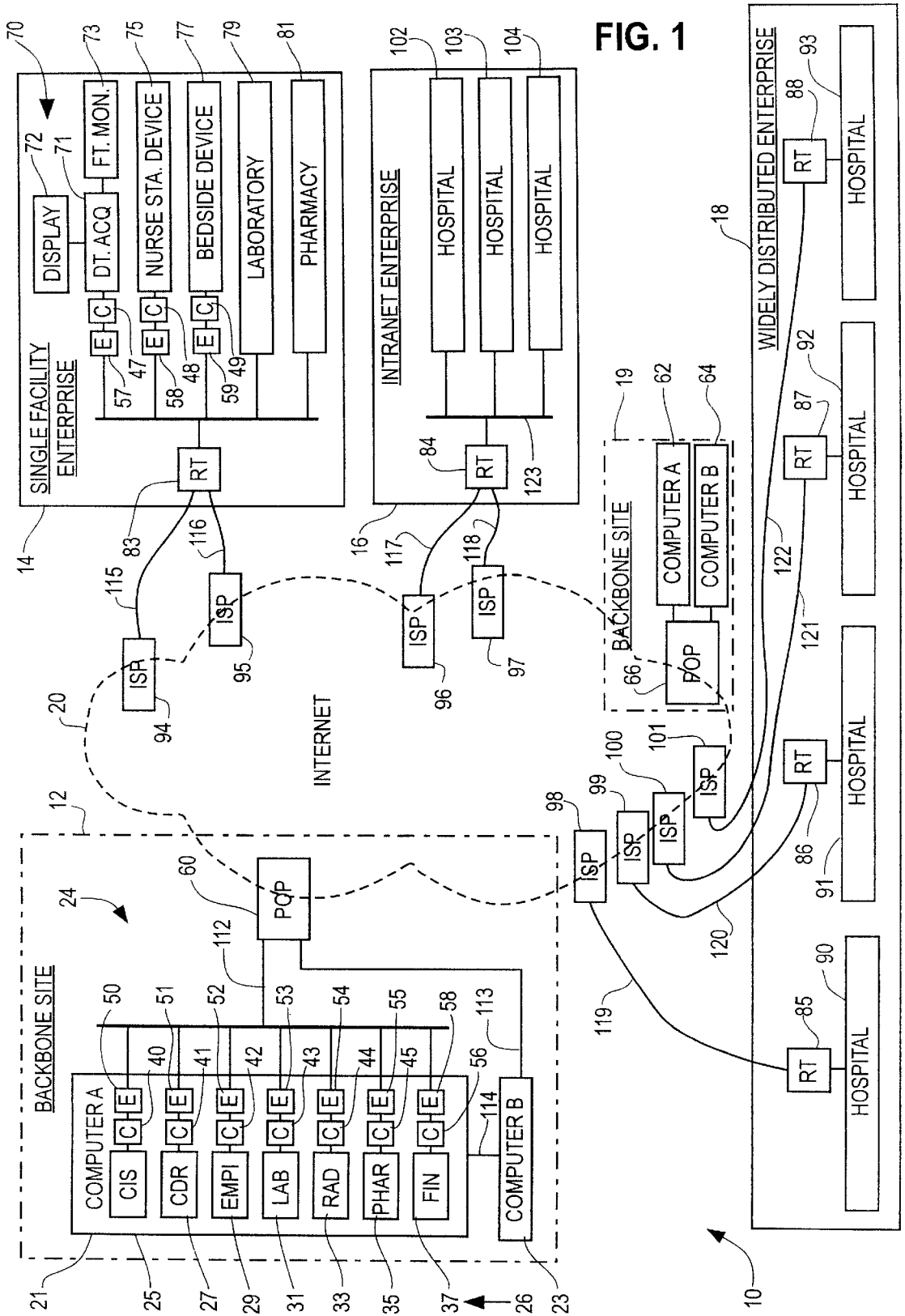
FIG. 1 is a block diagram showing an enterprise healthcare management system made in accordance with the present invention.

Referring now to the drawings, and more particularly to FIG. 1 thereof, there is shown a new enterprise healthcare management system 10 which is constructed in accordance with the present invention. The enterprise healthcare management system 10 is for use in healthcare enterprises comprising one or more facilities. These facilities, for example, may provide a point-of-care for healthcare patients.

The enterprise healthcare management system 10 generally comprises a redundant application server 24 accessing the Internet at a backbone site 12 through point of presence 60. Such a redundant system linking to the Internet at a major point of presence provides an extremely high quality of service for any remote user accessing the application server 24. Further, application server 24 has compression and encryption systems for authorizing users and securing communications. Healthcare enterprises are established in differing physical and administrative configurations. For example a health care enterprise may be configured as a single facility enterprise 14, an Internet enterprise 16, or a widely distributed enterprise 18. These health care enterprises connect to the Internet via an Internet service provider (ISP). In such a manner care providers at healthcare enterprise facilities communicate with the application server in a high-quality and secure manner.

In operation the redundant application server 24 operates a suite of healthcare software applications 26 for managing a healthcare enterprise. The suite of healthcare software applications 26 comprise a turnkey health care management system that includes, for example, patient care, financial, and administrative applications. This turnkey solution operates at a single location remote from the healthcare enterprise. Via the Internet, users at healthcare enterprises interactively access applications in the suite 26 to perform patient, financial, or administrative tasks.

Since the enterprise is using the Internet to access the remotely hosted applications, the healthcare enterprise needs only computing resources sufficient to allow secure, quality access to the Internet. In such a manner healthcare enterprises can quickly and cost effectively begin using the advanced healthcare management software applications in the turnkey suite of applications 26.

Further, since the turnkey suite of software applications 26 is running at a single location, the information collected from the enterprise for all applications may be stored in a searchable database. In such a manner a healthcare enterprise can monitor performance by generating reports comprising patient care, financial, and administrative information. Not only can such reports be generated for a single enterprise, but information from multiple enterprises can be aggregated to produce health industry wide performance reports.

Of course, a healthcare enterprise may already be successfully using a healthcare management application, for example, such as a financial application. If the healthcare enterprise desires to continue to use such a legacy program, the financial information from the legacy program is simply transmitted to the database and stored therein. Thereby a healthcare enterprise may continue to use a legacy financial program, but the data from the legacy program is still available to the enterprise healthcare management software for producing reports comprising multi-disciplinary information. This implementation flexibility further enables the turnkey enterprise healthcare management system 10 to efficiently manage different types of healthcare enterprises.

The healthcare management system 10 can be used whether the enterprise is a single facility enterprise 14 or a larger healthcare enterprise already interconnected with an intranet. Indeed the system is even flexible enough to manage a widely distributed enterprise 18 where multiple hospital facilities are not presently interconnected.

Referring again FIG. 1, components of the enterprise healthcare management system will be described in more detail. The Internet 20 is the world's most widely deployed network. The Internet 20 interconnects thousands of computers from around world. The Internet 20 uses a sophisticated addressing protocol to route information through the network. Since the particular path that electronic data may take when routed through the Internet is not known, the Internet 20 is typically represented as a cloud. In such a manner information is accepted into the Internet 20 at one location, routed through various Internet servers within the cloud, and then received at a final location.

Access to the Internet may be provided by an Internet service provider (ISP), such as Internet service providers 94–100. For a fee the Internet service provider establishes an Internet address for a user. In such a manner that user is then able to send and receive information via the Internet 20.

The Internet service provider typically contracts with a communication provider, such as the local phone company, to provide a high speed communication line. The high speed line may be, for example, a DS-3 communication line. The Internet service provider connects the high-speed communication line to network hardware used to route Internet messages. This network hardware, which may be a router or switch, provides the Internet service provider with a point of presence on the Internet.

The Internet service provider also typically provides a server connected to the network hardware. The server may contain content such as textual, video, or music information accessible to others on the Internet. Further, this server will handle the administrative tasks associated with managing subscribers to the Internet service provider.

As described above the Internet service provider has a point of presence on the Internet provided by a communication provider such as the local phone company. The reliability of the Internet service provider's service therefore is limited by the quality of the communication line, the local phone company, and the communication line used by the local phone company. The highest reliability communication lines are typically operated by the major communication companies such as MCI, AT&T, Sprint, and other national carriers. These national carriers have central office facilities where high-capacity communication lines terminate. These high-capacity communication lines are often called the backbone of the Internet. Regional and other smaller Internet service providers then connect to the central office backbone in a hierarchical manner. Since access to the backbone is provided at a central office for a major carrier, such access is provided at the highest possible quality of service level.

Backbone site 12 has an application server 24 and point of presence 60. This backbone site will be placed in close proximity to a termination point for the Internet backbone. For example, backbone site 12 may be a room leased from MCI at an MCI central office. Alternatively the backbone site may be separately placed close to the central office facility with a high-capacity communication line directly connected to the central office facility. Whether in the central office facility or proximately placed, the high-capacity communication line from the central office facility connects to the point presence hardware 60 at the backbone site 12. The point of presence hardware 60 may be a router, switch, or other hardware appropriate to provide a point presence on the Internet 20.

The application server 24 at the backbone site 12 is a redundant computer system. The redundant computer system is shown as application server 24 and comprises computer A 21 interconnected with computer B 23. Computer A connects to computer B through communication link 114. Computer A connects to the point of presence 60 through communication line 112. Computer B connects to the point of presence 60 through another communication line 113. In such a manner each computer has a separate access to the Internet, thereby increasing the reliability of the application server 24. To further increase reliability, computer B could connect to the Internet 20 through a separate point of presence. Due to its redundant nature and close proximity to the Internet backbone, application server 24 has a very high quality of service.

The application server 24 operates a suite of software applications 26 for turnkey healthcare management at a healthcare enterprise. This suite of software applications 26 includes a clinical information system 25 for providing day-to-day patient management functions. For example the clinical information system 25 provides automated clinical flow sheets for planning and tracking specific care given to a patient. The application suites 26 may also include laboratory software 31. The laboratory software 31 provides administrative functions for managing and tracking procedures at a clinic or hospital laboratory. In a similar manner radiology software 33 provides for the managing and tracking of radiology procedures for a patient. Pharmacy software 35 tracks both prescription and non-prescription drugs used by the patient. Financial software 37 provides accounting and asset management features necessary to operate a modern healthcare enterprise.

The application server 24 also has a clinical data repository 27. The clinical data repository 27 stores information from the other applications within the suite of applications 26. For example, the clinical data repository 27 will hold financial information as reported from financial software 37. The data repository 27 also stores pharmaceutical, radiology, laboratory, and clinical information data utilized by the other applications of the application suite 26. In such a manner the clinical data repository 27 stores multi-disciplinary information on a wide variety of enterprise functions. With such a repository of information, sophisticated reports on enterprise performance are easily generated. Although the application suite 26 has been shown with selected software applications, those skilled in the art will recognize that other applications may be used or substituted. For example, the suite of software 26 may include administrative software such as word processing.

The application software suite 26 also includes an Enterprise Master Patient Index (EMPI) for managing access to the application server 24. The EMPI has authorization and security information for establishing access rights for users. Further, the EMPI has basic patient information for assuring that information entered into any application is related to a valid patient.

Further enhanced security access to the application server 24 is provided through compression and encryption functions. These compression and encryption functions may also be provided at user devices in the healthcare enterprise. Compression functions, such as compression functions 40–49, not only add another layer of security to transmissions, but also make communications more efficient. Encryption functions, such as encryption functions 50–59, enable sensitive electronic data to be passed through the public Internet 20. Such sensitive data is encrypted at one end of the transmission and then decrypted at the other end of the transmission for secure communication. For example, a user at the nurse station device 75 of the single facility enterprise 14 desires to send sensitive clinical patent data related to a patient to the financial application 37. Security is established between the nurses station device and the application server before any sensitive data is transmitted.

In establishing security the encryption functions 58 at the nurses station 75 communicates with the encryption function 56 at the application server 24. The encryption functions 56 and 58 perform a handshaking procedure whereby agreement is reached on the type of encryption to use. Preferably security is established pursuant to the SecureIP standard. The SecureIP standard is an emerging standard for virtual private networks for providing a point-to-point connection between a server and an end user device. This point-to-point connection is often called a "tunnel". Once the secure tunnel is created, the sensitive information is transmitted.

The redundant computer system A communicates with various enterprise devices, such as nurse's station device 75 and bedside device 77. To increase system efficiency and reliability, Computer A 21 and computer B 23 share the interactive workload. For example, nurses station device 75 establishes communication with computer A 21. In such a manner an application running on computer A interacts with the nurse's station device 75 to perform a day-to-day function. Computer A 21 communicates selected information to computer B 23 so that computer B 23 could take responsibility for nurse's station 75 if computer A 21 fails. However, bedside device 77 established communication with computer B 23. An application running on computer B interacts with the bedside device 77 to perform a day-to-day function. Computer B 23 communicates selected information to computer A 21 so that computer A could take responsibility for bedside device 77 if computer B fails. Thus, in normal operating mode, computer A and computer B are each assigned primary responsibility for only selected devices.

At the backbone site 12, the application server 24 is shown as a single redundant computer system. Those skilled in the art will recognize that multiple computers could be used. For example, each application in the suite of applications 26 could be operated on a separate computer, thereby resulting in a set of redundant computers. In such a manner system reliability and throughput could be increased. Alternatively selected functions could be removed from a main redundant computer and placed on another redundant system. For example, a separate redundant computer system could be used for managing the clinical data repository 27 and the associated database functions.

FIG. 1 shows backbone site 19 having redundant computers 62 and 64 accessing the Internet via point presence 66. The backbone site 19 thereby provides service to healthcare enterprises geographically near backbone site 19.

Backbone site 19 may also provide full or partial backup functionality to backbone site 12. Thereby, if a catastrophic failure strikes backbone site 12, healthcare enterprises serviced by backbone site 12 will have some or all of their functionality transferred to backbone site 19. In such a manner overall system integrity is increased.

As generally described above, the turnkey healthcare management system 10 has the flexibility to effectively and efficiently operate differing types of healthcare enterprises. For example, the healthcare management system 10 may be used to operate a single facility enterprise 14. The single facility enterprise 14 is typically a single stand-alone hospital. The hospital may already have an existing network in place such as network 132. To use the healthcare management system 10, the single facility enterprise 14 obtains access to the Internet through a networking device 83 coupled to Internet service providers 94 and 95. The networking device 83 may be, for example, a switch or router coupling to the enterprise's existing network. The networking device 83 couples to the first ISP 94 through a communication link 115. The networking device 83 establishes a second link to the Internet using communication line 116 connected to Internet service provider 95. By providing two independent Internet service providers and communication links, system reliability is enhanced. Quality of service could be further increased by adding a second independent networking device for connecting to the second Internet service provider 95.

The single facility enterprise 14 comprises several devices needing to send and receive information to the turnkey healthcare management system 10. For example, as described above, a nurse at nursing station device 75 may need to access one or more of the applications operating on the application server 24. In a similar manner there may be a bedside device 77, such as a data display terminal, for sending information to and from the clinical information system 25 operating on the application server 24.

The single facility enterprise 14 also has automated monitoring devices such as fetal monitor 70. The fetal monitor device 70 has a fetal monitor 73 attached to a patient. The fetal monitor operates locally to collect, analyze, and present information so that immediate local medical decisions can be made. Information collected or processed at the fetal monitor 73 is passed to data acquisition device 71. Information may be displayed locally on display 72. Periodically the fetal monitor device 70 establishes a secure tunnel to an application running on the application server 24. After the tunnel is established, the fetal monitor device 70 transmits data and processed information to, for example, the clinical information system 25. In such a manner the fetal monitor device 70 operates in a local mode but still provides data for inputs into the remote applications.

As shown in FIG. 1, single facility enterprise 14 already has legacy laboratory software 79 and pharmacy software 81. Thereby the single facility enterprise does not need the laboratory software 31 or pharmaceutical software 35 operating on the application server to perform day-to-day operations. However the information collected and used locally in the laboratory 79 and pharmacy 81 software is provided to the central data repository 27 at the application server 26. In such a manner the database of information relating to the single facility enterprise 14 contains complete information even if the enterprise does not use all the applications in the suite of applications 26. Therefore, even if using legacy applications, multidisciplinary reports indicative of enterprise performance can still be generated.

A healthcare enterprise may comprises several point of care facilities interconnected with an intranet. For example, intranet enterprise 16 comprises hospital 102, hospital 103, and hospital 104 connected with the intranet 123. Although the intranet enterprise 16 is shown having separate hospital facilities, these point of care facilities may also include clinics, laboratories, or pharmacies. The intranet enterprise 16 also accesses the Internet via dual Internet service providers, as described above. Thereby hospitals 102–104 access the Internet through networking device 84 which couples to Internet service provider 96 via communication link 117. A second Internet service provider 97 connects to networking device 805 through communication line 118. Each hospital or point of care facility within the intranet enterprise 16 may thereby utilize applications in the turnkey software suite 26 as previously described. Information relating to the intranet enterprise 16 is separately stored in the central data repository 27. In such a manner enterprise wide reports can be generated showing the intranet enterprise 16 performance.

Another type of healthcare enterprise is the widely distributed enterprise. The widely distributed enterprise 18 has point of care facilities geographically dispersed with no or limited computer interconnection. For example, widely distributed enterprise 18 shows four point of care hospitals 90–93 each having a networking device 85–88 connected to Internet service providers 98–101 through communication links 119–122. Thereby each hospital may utilize applications in the software suite 26 for performing day-to-day operations as previously described. A separate partition of the clinical data repository 27 is established for the widely distributed enterprise 18. In such a manner managers of the widely distributed enterprise 18 can generate reports on enterprise wide performance.

The clinical data repository 27 thereby has multiple partitions, with each partition holding healthcare management information for an enterprise. In such a manner reports can be generated indicating the performance of a single enterprise. Further, reports can be generated encompassing multiple enterprises. In such a manner the data and information stored for each enterprise is aggregated with information stored for other enterprises for producing system wide reports. Using such system wide reports, an enterprise can compare its performance against other healthcare enterprises.

Figure 2:
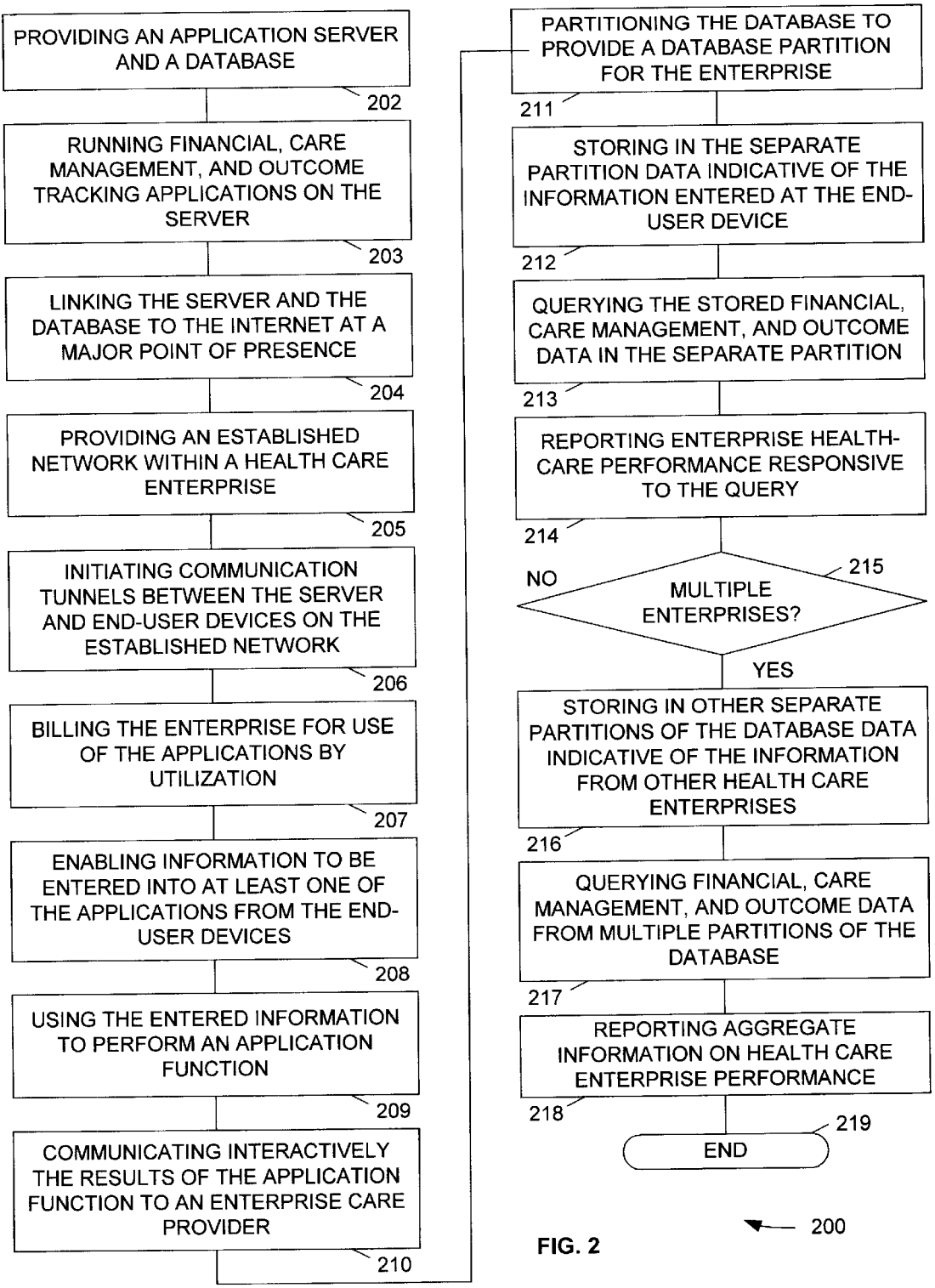
FIG. 2 is a flowchart of a method using an enterprise healthcare management system in accordance with the present invention.

Referring now to FIG. 2 there is shown a method 200 of using a turnkey enterprise healthcare management system. The method begins in block 202 by providing an application server and a database as previously described. Block 203 shows that financial, care management, and outcome tracking applications operate on the application server. The outcome tracking application is for tracking and reporting patient results. In such a manner, the outcome tracking application tracks how long the patient stayed at a point of care facility, what the outcome of the specific treatment was, and what the long-term prognosis for the patient was. For example, the system can track if the patient died, got better, or came down with another ailment. Combined with other information in the database, the outcome information is used to generate performance reports.

Block 204 shows the application server and the database are connected to the Internet at a major point of presence. As described above this major point of presence is preferably at a backbone site. The healthcare enterprise has an established network as shown in block 205. Secure communication tunnels are established between the application server and end-user devices on the established network as shown in block 206. To use the healthcare management system, the enterprise need not invest substantial capital in computer hardware and software, but instead uses the healthcare management system on a fee basis. In such a manner block 207 shows that the enterprise is billed for the applications as utilized.

Block 208 shows that information is entered into one of the applications running on the application server from an end-user device. The entered information is used to perform an application function as shown in block 209. At this point, the end-user and the application server are communicating interactively to perform a day-to-day function as shown in block 210.

The clinical data repository is a database that is partitioned to provide a database partition for an individual enterprise as shown in block 211. The database portion may be configured as either a logical partition or a physical partition, although a logical partition is preferred. Information entered into any of the applications running on the application server for that particular enterprise are stored in the database partition as shown in block 212. This separate partition, which contains multidisciplinary information such as financial, care management, and outcome data, is queried with a database search engine as shown in block 213. Block 214 shows that reports are generated indicating enterprise healthcare performance responsive to the query.

The healthcare management system is capable of supporting multiple enterprises. If multiple enterprises are operated as shown in block 215, then the information related to each of the separate healthcare enterprises is stored in a separate partition of the database as shown in block 216. The database engine can then be used to query across multiple database partitions as indicated in block 217. Block 218 shows that aggregate information can then be reported on the performance all managed multiple enterprises. The process then ends in block 219.

Figure 3:
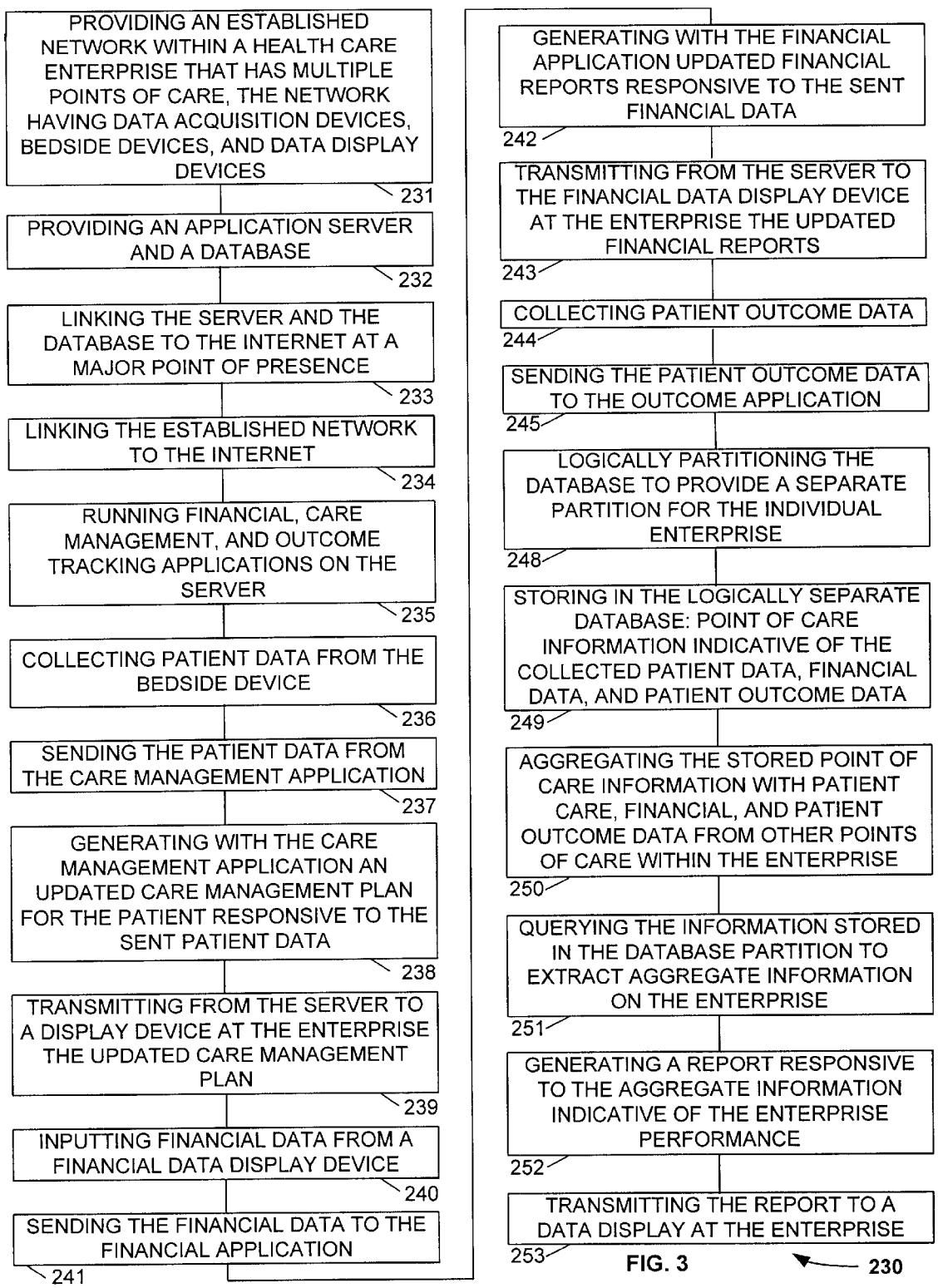
FIG. 3 is a flowchart of another method using an enterprise healthcare management system in accordance with a present invention.

Referring now to FIG. 3, another method 230 using the healthcare management system is shown. Method 230 starts in block 231 with an established healthcare network. The established healthcare network is within a healthcare enterprise that has multiple points of care. The established healthcare network has data acquisition devices, bedside devices, and data display devices. Block 232 shows that an application server and a database is provided, with block 233 showing that the server and database are linked to the Internet at a major point presence. As described before, block 234 shows linking the established network to the Internet. Financial, care management, outcome tracking applications are operating on the server as shown in block 235. Those skilled in the art will recognize other applications may be added or substituted.

Patient data is collected from a bedside device as shown in block 236. The collected data is sent via the Internet to the care management application operating on the application server as shown in block 237. Based on the information collected from the bedside device, the care management application operating on the application server generates an updated care management plan for the patient as shown in block 238. The updated care management plan is transmitted from the application server to a display device at the enterprise as shown in block 239. In such a manner care providers at the enterprise can use the updated care management plan for providing care to the patient.

Using a data display device at the enterprise, a user inputs financial data into the device as shown in block 240. The financial data is sent via the Internet to the financial application operating on the application server as shown in block 241. Financial reports are generated by the financial application responsive to receiving financial information as shown in block 242. These financial reports are transmitted from the server back to the financial data display device at the enterprise for presenting updated financial reports as shown in block 243. In such a manner the enterprise may use the financial software operating on the application server to run the day-to-day financial operations of the healthcare enterprise.

In block 244 patient outcome data is collected. The patient outcome data is sent via the Internet to an outcome application operating on the application server as shown in block 245. The outcome application operating on the server may be part of the care management application discussed above, or may be a discrete application. In such a manner users at the healthcare enterprise uses application server software to handle day-to-day outcome patient tracking.

The application server has a database for storing data and information relating to the healthcare enterprise. The database is logically partitioned for storing data relating to that enterprise in a separate partition as shown in block 248. The logical database partition is used to store collected patient data, financial data, patient outcome data, and other information related to care given a patient as shown in block 249. Block 250 shows that patient care data, financial data, and other data is aggregated with other points' of care information within the enterprise so that thee logical database partition has data reflecting care throughout the enterprise. This database may then be queried with a database engine to extract aggregate information on enterprise performance as shown in block 251. Block 252 shows that reports are generated responsive to the aggregate information for showing enterprise performance. These reports are then transmitted to the enterprise for review as shown in block 253.

Figure 4:
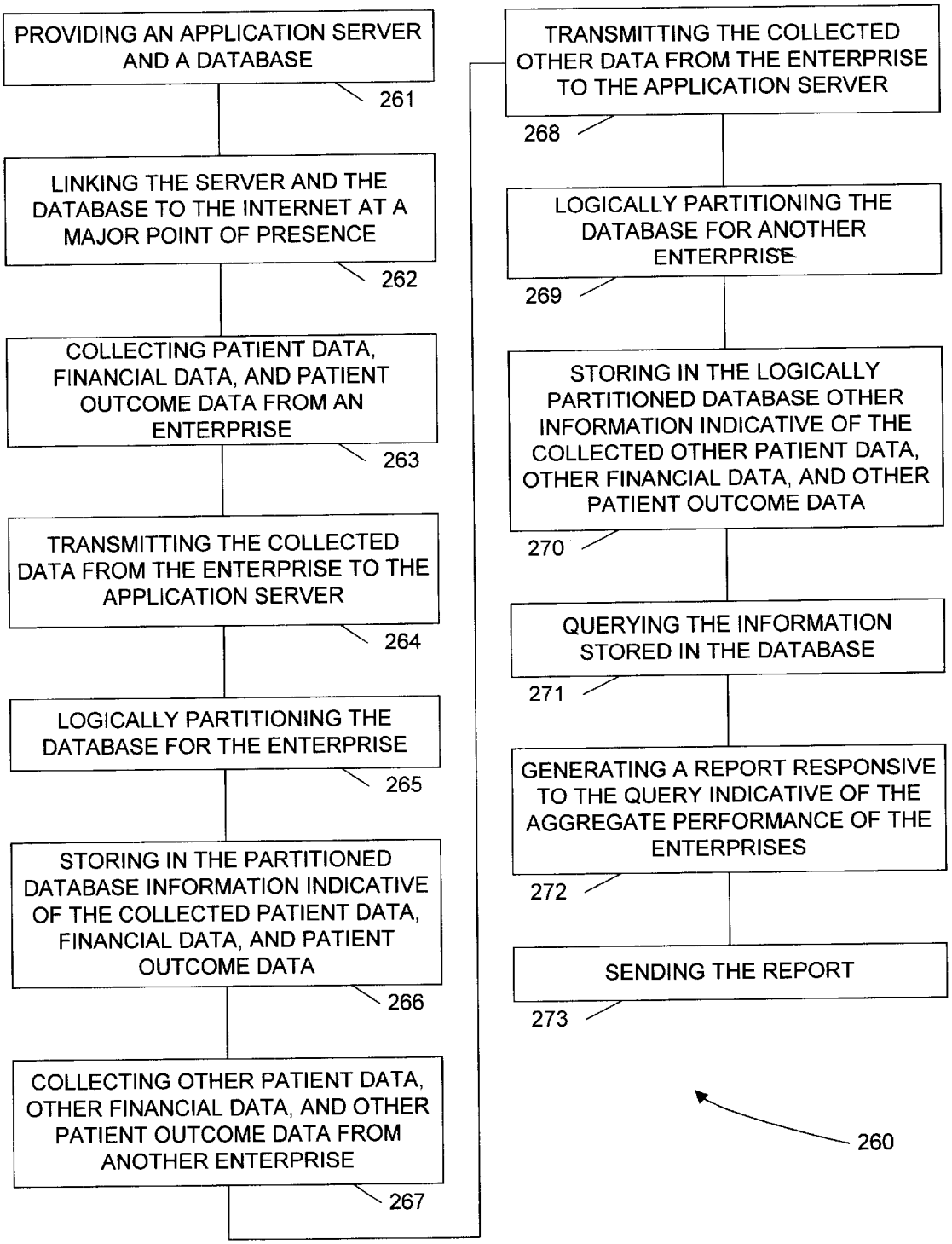
FIG. 4 is a flowchart of yet another method using an enterprise healthcare management system in accordance with the present invention.

Referring now to FIG. 4 there is shown a method 260 for using the healthcare management system for multiple enterprises. Block 261 and 262 show that the application server and database are connected to the Internet at a major point of presence. Blocks 263 and 264 show that patient data, financial data, and patient outcome data is collected from an individual enterprise and transmitted to the application server. As described earlier, the database is logically partitioned for storing enterprise data into a separate partition as shown in blocks 265 and 266.

Block 267 shows that similar types of data is collected from other enterprises. The data collected from the other enterprises is transmitted to the application server as shown in block 268 and stored in other logical database partitions as shown in blocks 269 and 270. The database may then query information stored in all partitions as shown in block 271. Reports are generated responsive to the query indicative of the aggregate performance of all enterprises tracked by the system as shown in block 272. Block 273 shows the report is then sent to a requesting party. Thereby performance reports reflecting all subscribing enterprises can be generated.

Figure 5:
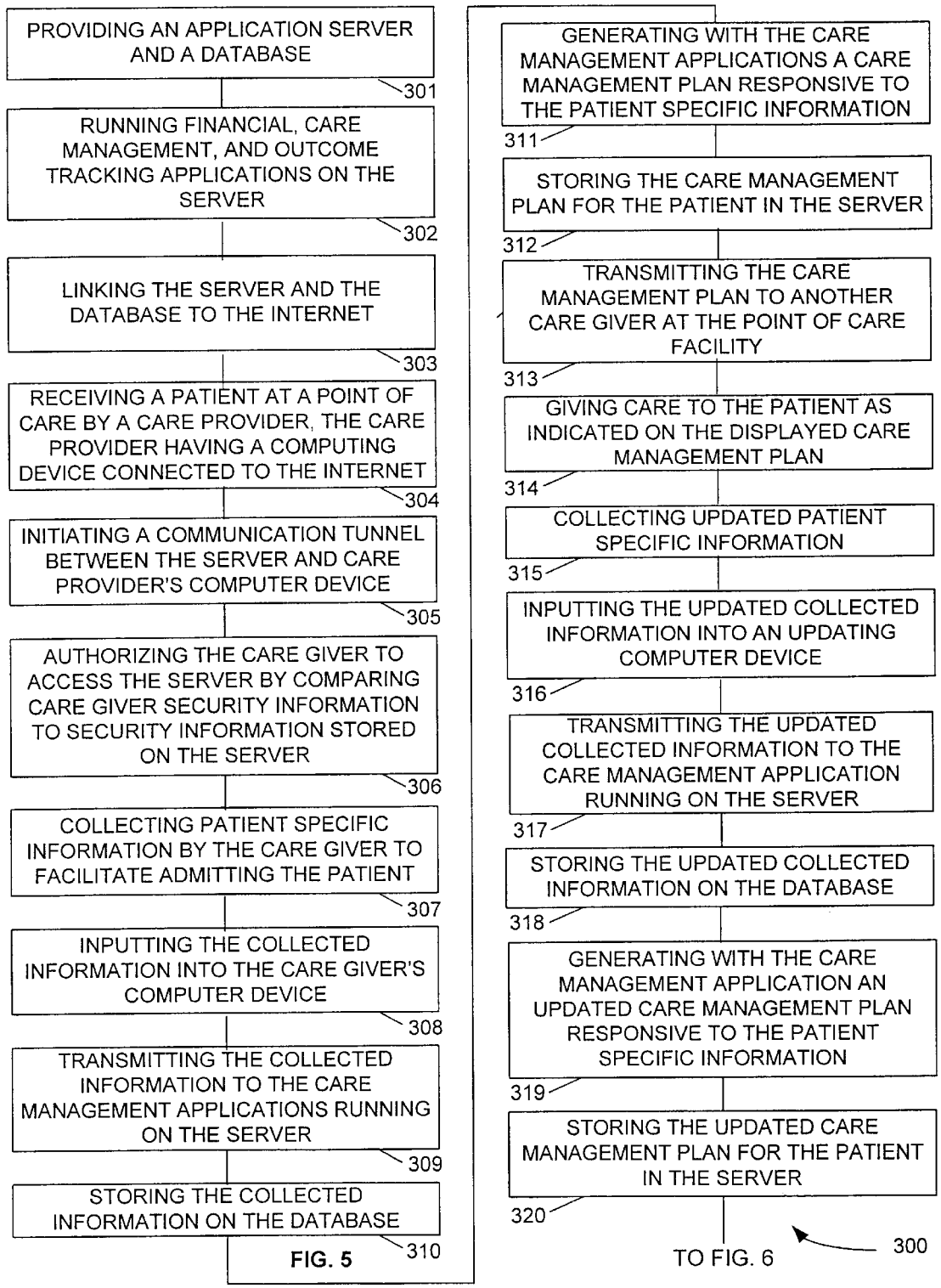
FIG. 5 is a flowchart of how an enterprise healthcare management system made in accordance with the present invention uses information relating to a patient.

Referring now to FIG. 5 another method 300 of using an enterprise healthcare management system is shown. Method 300 provides an application server and a database in block 301 for running financial, care management, outcome tracking applications as shown in block 302. The application server and database are linked to the Internet at major point presence is shown in block 303. A patient is received at a point of care facility, such as a hospital, by a care provider. The care provider has a computing device connected to the Internet as shown in block 304. The care provider initiates a communication tunnel to the application server and the care providers computing device as shown in block 305. The application server has a database of security information stored in the EMPI. The EMPI information is compared with information received from the caregiver's terminal device to authorize the care giver to access the application server as shown in block 306.

Once authorized to access the application server, the caregiver collects patient specific information to facilitate admitting the patient as shown in block 307. The caregiver inputs collected information into the caregivers computer device in block 308 with information being transmitted to the care management application running on the application server as shown in block 309. The information collected from the patient, or information derived from the collected information, is stored in the database residing at the application server as shown in block 310. The care management applications running on the server generate a care management plan responsive to the patient specific information entered by the caregiver as shown in block 311. This care management plan is also stored on the application server as shown in block 312.

The care management plan is transmitted to another caregiver at the point care facility as shown in block 313. This caregiver could be a doctor or nurse responsible for providing care or medication to the patient. The caregiver gives care to patient as indicated on the care manager plan as shown in block 314.

A caregiver at the point of care facility then collects updated patient specific information relating to patient status or care given to the patient as shown in block 315. This updated patient specific information is input into an updating computer device connected to the application server as shown in block 316. The updated collect information is transmitted via the Internet to the care management application running on the server as shown in block 317 and the data is stored on the database at the application server as shown in block 318. The care management application running on the application server prepares an updated care management plan responsive to the updated patient specific information as shown in block 319. The updated care manager plan is also stored at the database of the application server as shown in block 320.

Figure 6:
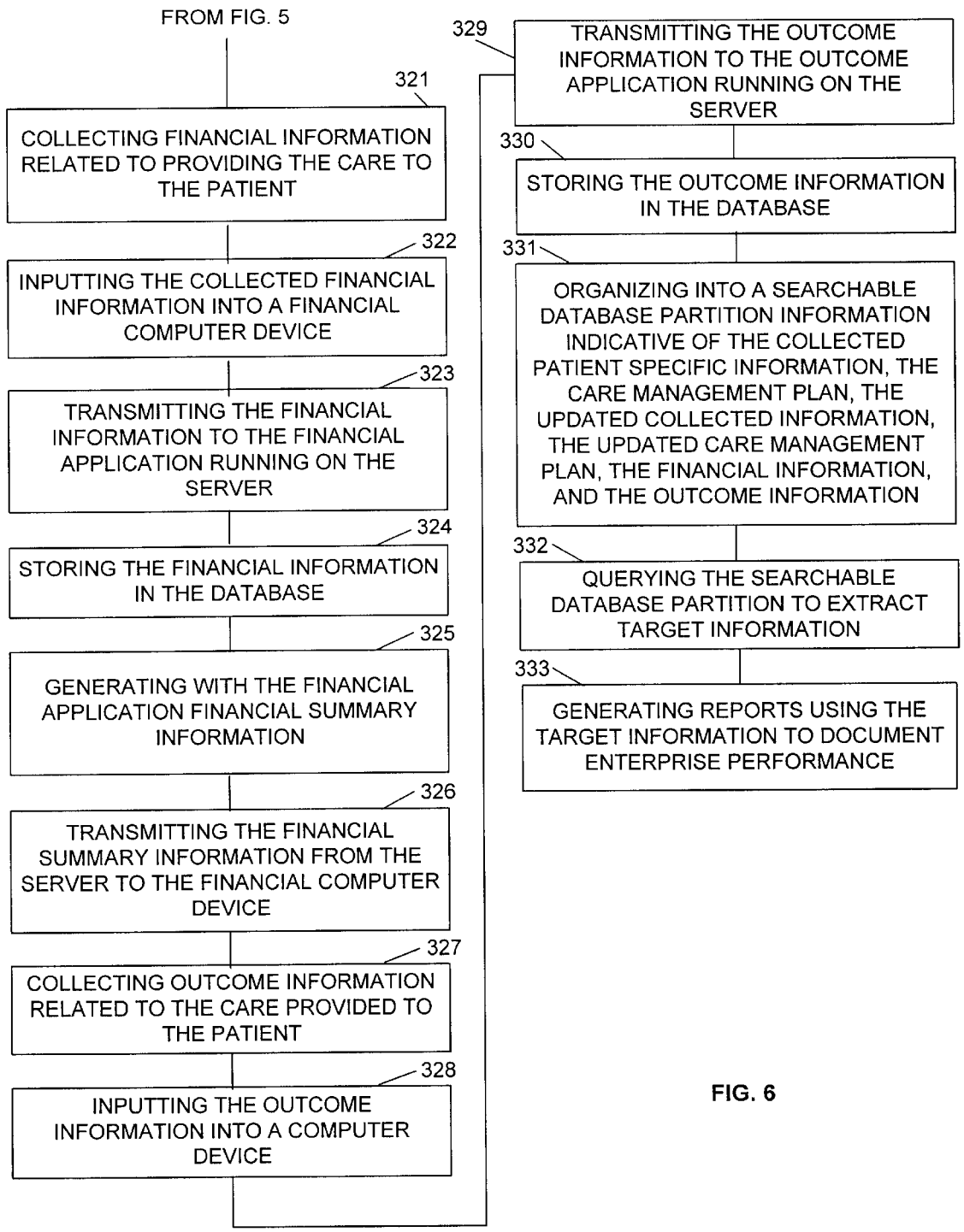
FIG. 6 is a continuation flowchart of FIG. 5.

Referring now to FIG. 6, which is a continuation of the flowchart of FIG. 5. Financial information relating to providing care for the patient is collected as shown in block 321. This collected financial information is input into a financial computing device as indicated in block 322. The financial information is transmitted to the application server where it is accepted by the financial application running on the server as shown in block 323. The financial information or information derived therefrom is stored in the database at the application server as shown in block 324. The financial application running on the server generates financial summary information as shown in block 325 and transmits this financial summary information from the server back to financial computer device as indicated in block 326.

Outcome information is collected from the patient as shown in block 327. This outcome information is input into computer device, such as a data display device, in block 328 and transmitted to the outcome application running on the application server as shown in block 329. The outcome information is stored in the database at the application server as shown in block 330.

The database at the application server has a searchable database with multidisciplinary information contained therein. This information includes collected patient information, updated collected patient information, care manager plan, update care manager plan, financial information, and outcome information as shown in block 331. Those skilled in the art recognize other types of information or data may be stored in the database relating to patient care. This searchable database can be queried to extract target information relating to the patient and to the health care facility as shown in block 332. Reports can be generated using this target information to document enterprise and point care service performance as shown in block 333.

Figure 7:
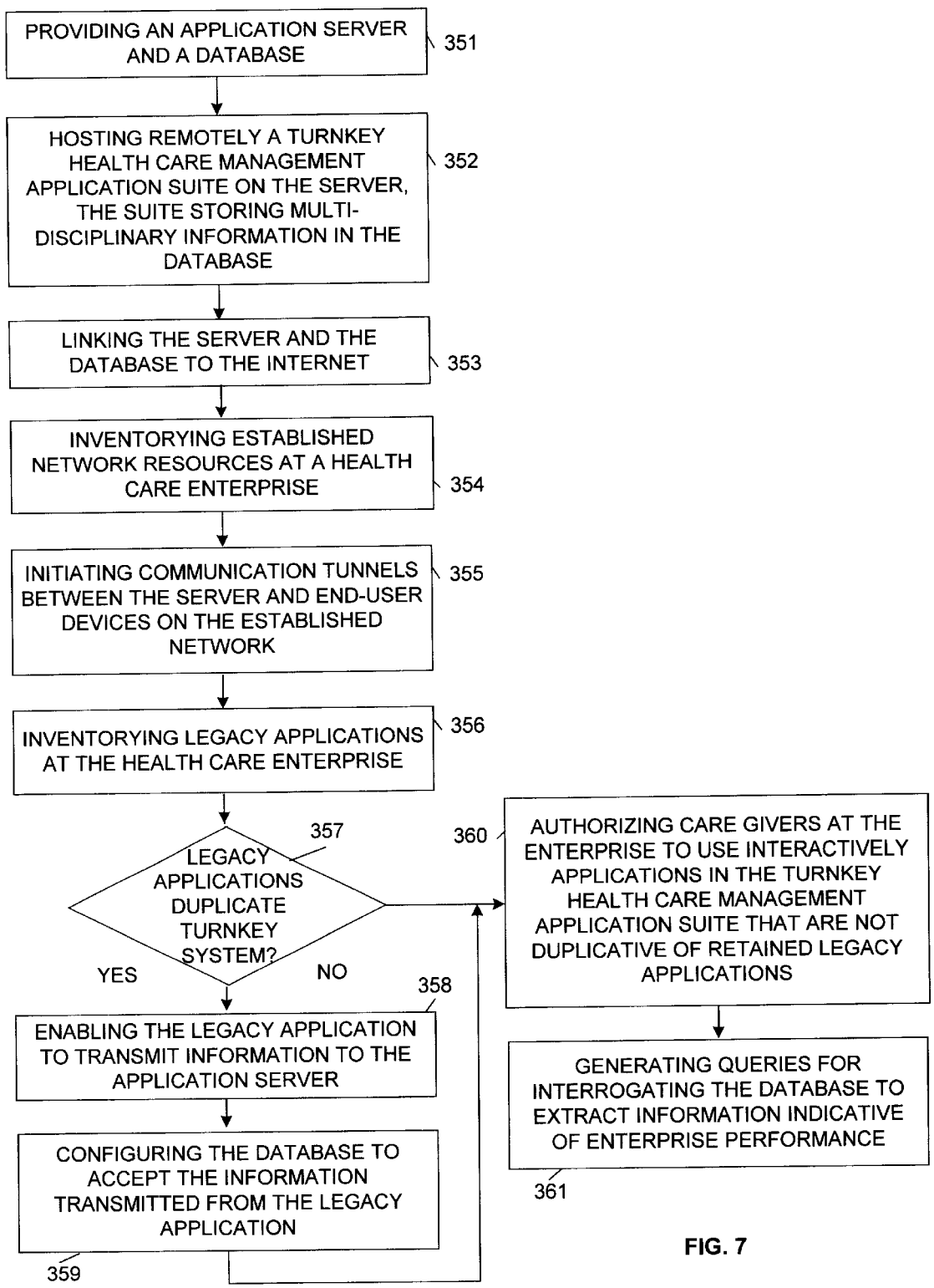
FIG. 7 is a flowchart of the process to install an enterprise healthcare management system made in accordance with the present invention.

Referring now to FIG. 7 a method 350 is shown for installing enterprise healthcare management system at an existing healthcare enterprise. Block 351 indicates that the installer provides an application server and a database. That application server remotely hosts turnkey healthcare management application suites, with the database storing multidisciplinary information as shown in block 352. The server and the database are linked to the Internet at major point presence as shown in block 353. The installer inventories established network resources to determine what network resources are available at the healthcare enterprise as shown in block 354. The installer installs the necessary hardware and software at the healthcare enterprise to initiate communication tunnels between the server and an end-user device on the established network as shown in block 355.

Since the healthcare enterprise may have legacy applications they wish to retain, the installer inventories legacy applications as shown in block 356. Block 357 queries if any of the retain legacy applications duplicate applications in the turnkey system. For example, the enterprise may desire to retain their existing financial system and therefore will not use the financial software in the server application suite. In such case the installer will enable the legacy application to transmit raw or processed information to the application server so that this information can be collected and retain for future report processing as shown in block 358. The database on the application server is configured to accept the information as transmitted from the legacy application as shown in block 359.

The installer then authorizes users at the healthcare enterprise to use interactively applications in the turnkey healthcare management application suite that are not duplicative of retained legacy applications as shown in block 360. In such a manner users at the healthcare enterprise can interactively use applications hosted on the application server for performing day-to-day patient and administrative functions for the healthcare enterprise. Finally in block 361 the installer uses a database searching engine to generate queries for interrogating the database to extract information indicative of enterprise performance. These queries are performed on multidisciplinary information to accurately portray enterprise performance.

The enterprise healthcare management system described above preferably uses the Internet for communication between the application server and the health care enterprise. However, the healthcare management system may use other public or private networks for establishing such communications. For example, the application server could be located proximate a health care enterprise and-directly couple to the enterprise's existing private network. Indeed, the application server could become a server on an enterprise's intranet network. In such a manner the application server remotely hosts the suite of health care applications, integrates with existing legacy applications, and generates multidiscipline enterprise performance reports. Similar to the implementation using the Internet, the enterprise can quickly and cost effectively utilize the enterprise healthcare management system.

Although the embodiments thus far described preferably utilize a suite of healthcare applications operating on the application server, other configurations are contemplated. The enterprise healthcare management system may offer a single application for use throughout the enterprise. In such a manner the enterprise can add new or augmented capabilities quickly and in a cost effective manner. For example, if a healthcare enterprise desires to add a care management application, such a care management application can be deployed enterprise-wide quickly, with little risk, and with minimal financial investment.

By using the enterprise healthcare management system and method disclosed herein, a healthcare enterprise can quickly and cost effectively generate critical decision support information. With such information, the healthcare enterprise is able to make informed decisions for improving financial performance while maintaining or improving patient care.

While particular embodiments of the present invention have been disclosed, it is to be understood that various different modifications are possible and are contemplated within the true spirit and scope of the appended claims. There is no intention, therefore, of limitations to the exact abstract or disclosure herein presented.

What is claimed is:

1. A method of operating an enterprise healthcare management system for a first healthcare enterprise facility and a second healthcare enterprise facility independent of the first healthcare enterprise facility, comprising:

establishing a first secure communication channel via a public network between an application server and a first end user device in the first enterprise facility and establishing a second secure communication channel via the public network between the application server and a second end user device in the second enterprise facility, the application server remotely hosting a healthcare application and having a database;

receiving first healthcare data from the first end user and second healthcare data from the second end user;

processing the first healthcare data and the second healthcare data with the healthcare application;

storing the processed first healthcare data in a first portion of the database associated with the first healthcare enterprise facility and storing the processed second healthcare data in a second portion of the database associated with the second healthcare enterprise facility;

configuring the database to accept legacy information derived from a legacy application operating at each of the first and second healthcare enterprise facilities, wherein the functions in the healthcare application are not duplicative of the legacy application; and generating a query to extract information from the database relevant to a respective one of the first and second healthcare enterprise facilities derived from the healthcare data and the legacy information for managing and tracking a performance of the respective one of the first and second healthcare enterprise facilities, wherein healthcare data in the first portion of the database is only accessible to the first end user device and healthcare data in the second portion of the database is only accessible to the second end user device.

2. The method of claim 1 further comprising providing a redundant application server.

3. The method of claim 1 wherein each of first and second enterprise facilities is part of a independent private network.

4. The method of claim 3 wherein each of the first and second enterprise facilities is part of an independent intranet.

5. The method of claim 1 wherein the public network is the Internet.

6. The method of claim 1 wherein an access point of the application server to the public network is a major point of presence on the public network.

7. The method of claim 1 further comprising installing the application server and the database proximate a central office facility for a communication carrier.

8. The method of claim 7 further including installing the application server and the database in the central office facility.

9. The method of claim 7 wherein the communication carrier is one selected from the group consisting of MCI, AT&T, and SPRINT.

10. The method of claim 1 wherein the healthcare application includes a financial application.

11. The method of claim 1 wherein the healthcare application includes a clinical information management application.

12. The method of claim 1 wherein the healthcare application includes an outcome application.

13. The method of claim 1 wherein the healthcare application includes a word processing application.

14. The method of claim 1 wherein the establishing step includes using a SecureIP handshaking protocol.

15. The method of claim 1 wherein the healthcare data is patient specific data for input to a clinical information system operating on the application server.

16. The method of claim 1 wherein the healthcare data is financial data for input to a financial application operating on the application server.

17. The method of claim 1 wherein the healthcare data is outcome data for input to an outcome application operating on the application server.

18. The method of claim 1 further including storing in the database information from multiple disciplines.

19. The method of claim 18 further including querying the stored multidiscipline data to generate reports on performance of one of the first and second enterprise facilities.

20. The method of claim 1 further including the step of storing in the database information received from a legacy program operating at one of the first and second enterprise facilities.

21. The method of claim 20 further including querying the stored healthcare data, including the legacy data, to generate reports on a performance of one of the first and second enterprise facilities.

22. The method of claim 1 further including collecting data from the healthcare data stored in the database from the first and second enterprise facilities to provide aggregate health care information.

23. The method of claim 22 further including running queries on the aggregate health care information to produce reports showing aggregate performance of the first and second enterprise facilities.

24. The method of claim 1, further comprising:
receiving a query from the first end user device;
querying only processed healthcare data in the first portion of the database in response to the query from the first end user device; and
generating a report based on a response to the query of the first portion of the database.

25. The method of claim 1, further comprising:
receiving legacy healthcare data processed by a legacy application in the first enterprise healthcare facility; and
storing the legacy healthcare data in the first portion of the database without processing the legacy healthcare data with the healthcare application.

26. A healthcare management system for a first healthcare enterprise facility and a second healthcare enterprise facility independent of the first healthcare enterprise facility, comprising:
an application server and a database, the application server remotely hosting one or more healthcare applications;
an application server and a database, the application server remotely hosting one or more healthcare applications;
an access point to a network at which the application server and link to a public network;
means for initiating secure communication between the application server and a first end user device at the first enterprise facility and for initiating secure communication between the application server and a second end user device at the second enterprise facility;
means for receiving healthcare data from the first and second end user devices at the one of the healthcare applications;
means for processing the received healthcare data; and
means for storing the processed healthcare data from the first end user device in a first portion of the database associated with the first enterprise facility and for storing the processed healthcare data from the second end user device in a second portion of the database associated with the second enterprise facility,
means for configuring the database to accept legacy information derived from a legacy application operating at each of the first and second healthcare enterprise facilities, wherein the functions in the healthcare application are not duplicative of the legacy application; and
means for generating a query to extract information from the database relevant to a respective one of the first and second healthcare enterprise facilities derived from the healthcare data and the legacy information for managing and tracking a performance of the respective one of the first and second healthcare enterprise facilities,
wherein healthcare data in the first portion of the database is only accessible to the first end, user device and healthcare data in the second portion of the database is only accessible to the second end user device.

27. The healthcare management system according to claim 26 further comprising a redundant application server.

28. The healthcare management system according to claim 26 further including means for operating the database on the application server.

29. The healthcare management system according to claim 26 wherein each of the first and second enterprise facilities is part of a private network.

30. The healthcare management system according to claim 29 wherein each of the first and second enterprise facilities is part of an intranet.

31. The healthcare management system according to claim 26 wherein the public network is the Internet.

32. The healthcare management system according to claim 26 wherein the access point is a major point of presence on the network.

33. The healthcare management system according to claim 26 wherein one of the healthcare applications includes a financial application.

34. The healthcare management system according to claim 26 wherein one of the healthcare applications includes a clinical information management application.

35. The healthcare management system according to claim 27 wherein one of the healthcare applications includes an outcome application.

36. The healthcare management system according to claim 26 wherein one of the healthcare applications includes a word processing application.

37. The healthcare management system according to claim 26 wherein the means for initiating includes means for establishing a virtual private network.

38. The healthcare management system according to claim 26 wherein the means for initiating includes a means for using the SecureIP handshaking protocol.

39. The healthcare management system according to claim 26 wherein the healthcare data is patient specific data for input to a clinical information system operating on the application server.

40. The healthcare management system according to claim 26 wherein the healthcare data is financial data for input to a financial application operating on the application server.

41. The healthcare management system according to claim 26 wherein the healthcare data is outcome data for input to an outcome application operating on the application server.

42. The healthcare management system according to claim 26 further including means for storing in the database information from multiple disciplines.

43. The healthcare management system according to claim 42 further including means for querying the stored multidiscipline data to generate reports on a performance of one of the first and second enterprise facilities.

44. The healthcare management system according to claim 26 further including the means for storing in the database information received from a legacy program operating at one of the first and second enterprise facilities.

45. The healthcare management system according to claim 44 further including means for querying the stored healthcare data, including the legacy data, to generate reports on a performance of one of the first and second enterprise facilities.

46. The healthcare management system according to claim 26, further comprising:

means for receiving a query from the first end user device;

means for querying only processed healthcare data in the first portion of the database in response to the query from the first end user device; and means for generating a report based on a response to the query of the first portion of the database.

47. The healthcare management system according to claim 26 further including means for installing the application server and the database proximate a central office facility for a communication carrier.

48. The healthcare management system according to claim 47 further including means for installing the application server and the database in the central office facility.

49. The healthcare management system according to claim 47 wherein the communication carrier is one selected from the group consisting of MCI, AT&T, and SPRINT.

50. A method of operating a healthcare management system, comprising:

hosting remotely on an application server a healthcare application configured to store application information in a database;

linking the application server and the database to a public network;

initiating secure communication between end user devices at an enterprise facility and the application server;

configuring the database to accept legacy information derived from a legacy application operating at the enterprise facility, wherein the functions in the healthcare application are not duplicative of the legacy application; and generating a query to extract information from the database derived from the application information and the legacy information for managing and tracking a performance of the enterprise facility.

51. The method of claim 50 wherein the public network is the Internet.

52. The method of claim 50 wherein the enterprise facility is a private network.

53. The method of claim 50 wherein the enterprise facility is an intranet.

54. The method of claim 50 wherein the linking step includes the server and the database to the network at a major point of presence.

55. The method of claim 50 wherein the healthcare application includes a plurality of applications.

* * * * *

UNITED STATES PATENT AND TRADEMARK OFFICE
CERTIFICATE OF CORRECTION

PATENT NO.        : 6,665,647 B1
APPLICATION NO.   : 09/343295
DATED             : December 16, 2003
INVENTOR(S)       : Chris A. Haudenschild Page 1 of 1

It is certified that error appears in the above-identified patent and that said Letters Patent is hereby corrected as shown below:

Title Page, Item (76), the correct current mailing address number "1769 La Jolla Rancho Rd., La Jolla, CA (US) 92037" should read -- 9655 Towne Centre Drive, San Diego, CA (US) 92121 --.

Signed and Sealed this
Twentieth Day of December, 2016

Michelle K. Lee
*Director of the United States Patent and Trademark Office*

(12) INTER PARTES REVIEW CERTIFICATE (2496th)
United States Patent
Haudenschild

(10) Number: US 6,665,647 K1
(45) Certificate Issued: Nov. 15, 2021

(54) ENTERPRISE HEALTHCARE MANAGEMENT SYSTEM AND METHOD OF USING SAME

(75) Inventor: Chris A. Haudenschild

(73) Assignee: CLINICOMP INTERNATIONAL, INC.

Trial Numbers:

IPR2018-01634 filed Aug. 31, 2018
IPR2019-00926 filed Apr. 5, 2019

Inter Partes Review Certificate for:

Patent No.: 6,665,647
Issued: Dec. 16, 2003
Appl. No.: 09/343,295
Filed: Jun. 30, 1999

The results of IPR2018-01634 joined with IPR2019-00926 are reflected in this inter partes review certificate under 35 U.S.C. 318(b).

INTER PARTES REVIEW CERTIFICATE
U.S. Patent 6,665,647 K1
Trial No. IPR2018-01634
Certificate Issued Nov. 15, 2021

AS A RESULT OF THE INTER PARTES REVIEW PROCEEDING, IT HAS BEEN DETERMINED THAT:

Claims 1-25 are found patentable.

Claims 50-55 are cancelled.

\* \* \* \* \*